United States Patent [19]

Resendez

[11] Patent Number: Plant 6,959

[45] Date of Patent: Aug. 1, 1989

[54] BOUGAINVILLEA HYBRID CV. MONKA

[75] Inventor: Gilbert N. Resendez, La Verne, Calif.

[73] Assignee: Monrovia Nursery Company, Azusa, Calif.

[21] Appl. No.: 240,803

[22] Filed: Sep. 6, 1988

[51] Int. Cl.[4] ..... A01H 5/00

[52] U.S. Cl. ..... Plt./54

[58] Field of Search ..... Plt./54

*Primary Examiner*—James R. Feyrer

[57] ABSTRACT

A new and distinct selection of Bougainvillea shrub which shall be referred to hereinafter as Bougainvillea hybrid cultivar Monka. Bougainvillea hybrid cultivar Monka differs distinctively from other bougainvillea plants by a unique combination of floriferous habit, dwarf mounding shape, and vibrant purple flower bracts.

1 Drawing Sheet

BACKGROUND OF THE NEW PLANT

This invention relates to a new and distinct selection of Bougainvillea, a member of the Nyctaginaceae or Four-O'Clock Family. Bougainvillea hybrid cv. Monka was discovered by me in a group of Bougainvillea hybrid cultivar Rosenka at Monrovia Nursery Company, 18331 E. Foothill Boulevard, Azusa, Calif. in the summer of 1985.

My new selection has been strictly asexually reproduced by cuttings at Monrovia Nursery Company. The distinct phenotypic characteristics of this new selection that set this plant apart from other bougainvillea plants could be lost genetically through sexual reproduction. Therefore, sexual reproduction is prohibited and propagation is restricted to asexual reproduction by cuttings. Seed progeny from the new selection has not been observed.

SUMMARY OF INVENTION

Bougainvillea hybrid cv. Monka is unique. To prove this uniqueness, a comparison of cv. Rosenka, the original cultivar and cv. Crimson Jewel, a cultivar of somewhat similar habit and color, shall be made.

The most obvious difference of cv. Rosenka and cv. Monka is the color of the flower bracts. The cv. Rosenka has color tones of pink and orange. The cv. Monka has color tones of vibrant purple. Though cv. Monka was selected from cv. Rosenka, the habit of cv. Monka tends to be more compact and more dense than cv. Rosenka. Cultivar Crimson Jewel also has purple flower bracts but the color is more red-purple, 729 Peony Purple, cultivar Monka is 30 Cyclamen Purple with more vibrant purple color. The peduncle on cultivar Crimson Jewel is always longer than the length of the bract, in most cases more than twice as long. The peduncle is rarely longer than the length of the flower bract on cultivar Monka.

BRIEF DESCRIPTION OF DRAWINGS

The accompanying illustrations show a typical specimen of the plant according to this invention and are depicted in color as nearly true as possible.

BOTANICAL DESCRIPTION

Figure 1:
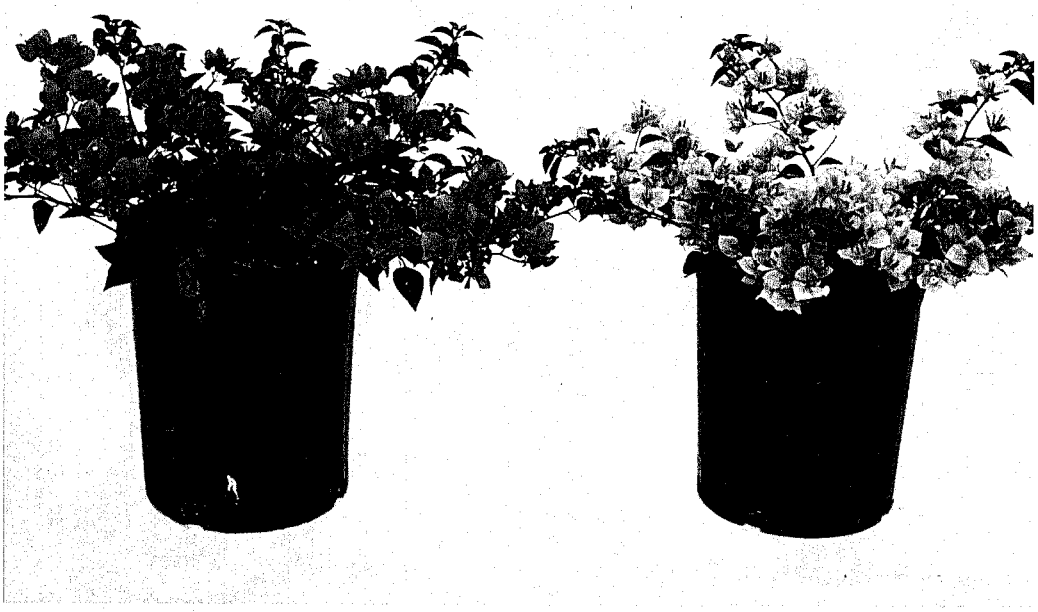
FIG. 1 depicts the overall habit of the original plant my sport was discovered on, cultivar Rosenka on the right and my new selection on the left. The dense, compact, floriferous habit of both the parent and my selection should be noted.
Figure 2:
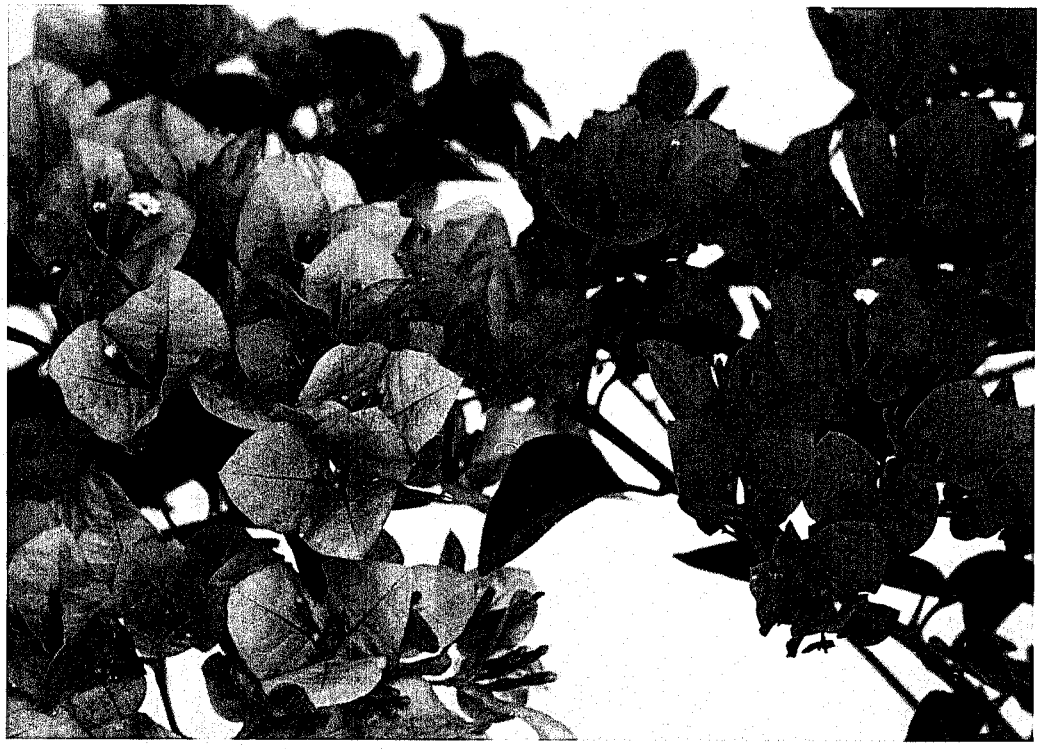
FIG. 2 exhibits the color difference of the flower bracts in the original plant, cultivar Rosenka on the left and cultivar Monka on the right.

Below is a detailed description of the new Bougainvillea hybrid cv. Monka, the color terminology is from The British Horticultural Colour Charts.

Overall size and habit: Evergreen foliage, dense mounding growth habit. After 5 years plant should achieve height of 2 feet tall with a spread of 4–6 feet.

Flower: Free flowering in Southern California from February to November.

- *Calyx.*—Tubular 1.7 cm long, (+ −2 mm) puberulent with five longitudinal ribs and five shallow lobes, color is Erythrite Red 0027.
- *Calyx petaloids.*—Five in number, attached to calyx lobes.
- *Arrangement.*—Flowers in clusters of three, each attached by the pedicel to one persistent showy bract.

Flower bract:

- *Color.*—Cyclamen Purple 30.
- *Size.*—Length 2.5 cm–3.7 cm; width 2.0 cm–2.8 cm.
- *Shape.*—Widely elliptic.
- *Margins.*—Undulate.

Leaf:

- *Arrangement.*—Alternate
- *Size.*—Foliage size varies considerably depending on if on older wood or on young rapidly growing branches — length 3.5 to 5.5; width 2.1 to 4 cm.
- *Color.*—Lower surface: Spinach Green 0960/2; upper surface Spinach Green 0960.
- *Shape.*—Ovate.
- *Margins.*—Entire.
- *Pubescense.*—Puberulent on upper and lower leaf surfaces Fruit: not significant, not observed.

I claim:

1. A new and distinct selection of Bougainvillea as substantially shown and described herein, that is characterized particularly as a novelty by the unique combination of floriferous habit, dwarf mounding shape, and vibrant purple flower bracts.

* * * * *